US012611437B2

(12) United States Patent
Choung

(10) Patent No.: US 12,611,437 B2
(45) Date of Patent: \*Apr. 28, 2026

(54) **COMPOSITION FOR PREVENTING OR TREATING TINNITUS COMPRISING *VITIS VINIFERA* LEAF EXTRACT AS ACTIVE INGREDIENT**

(71) Applicant: AJOU UNIVERSITY INDUSTRY-ACADEMIC COOPERATION FOUNDATION, Suwon-si (KR)

(72) Inventor: Yun-Hoon Choung, Seoul (KR)

(73) Assignee: AJOU UNIVERSITY INDUSTRY-ACADEMIC COOPERATION FOUNDATION, Suwon-si (KR)

( \* ) Notice: Subject to any disclaimer, the term of this patent is extended or adjusted under 35 U.S.C. 154(b) by 1087 days.

This patent is subject to a terminal disclaimer.

(21) Appl. No.: 17/429,543

(22) PCT Filed: Feb. 12, 2020

(86) PCT No.: PCT/KR2020/001964
§ 371 (c)(1),
(2) Date: Aug. 9, 2021

(87) PCT Pub. No.: WO2020/166962
PCT Pub. Date: Aug. 20, 2020

(65) Prior Publication Data
US 2022/0133832 A1 May 5, 2022

(30) Foreign Application Priority Data

Feb. 12, 2019 (KR) ........................ 10-2019-0015991

(51) Int. Cl.
*A61K 36/87* (2006.01)
*A23L 33/00* (2016.01)
(Continued)

(52) U.S. Cl.
CPC ............ *A61K 36/87* (2013.01); *A23L 33/105* (2016.08); *A23L 33/40* (2016.08); *A61P 27/16* (2018.01);
(Continued)

(58) Field of Classification Search
CPC . A61K 36/87; A61K 2236/333; A23L 33/105; A23L 33/40; A61P 27/16; A23V 2002/00; A23K 2236/331
See application file for complete search history.

(56) References Cited

FOREIGN PATENT DOCUMENTS

| CN | 105192782 A | \* 12/2015 |
| JP | 2004-238289 A | 8/2004 |

(Continued)

OTHER PUBLICATIONS

Machine translation of CN-105192782-A from PE2E via FIT (Year: 2015).\*

(Continued)

*Primary Examiner* — Craig D Ricci
*Assistant Examiner* — Ayaan A Alam
(74) *Attorney, Agent, or Firm* — Sughrue Mion, PLLC

(57) ABSTRACT

A composition containing a *Vitis vinifera* leaf extract as an active ingredient and its uses in preventing or treating tinnitus are disclosed. The composition may be a pharmaceutical composition or a food composition. The composition containing a *Vitis vinifera* leaf extract as an active ingredient is excellent in alleviating and improving tinnitus caused by noise and the like, and therefore is very useful as a composition for preventing or treating tinnitus.

4 Claims, 4 Drawing Sheets

(51) Int. Cl.
  *A23L 33/105*     (2016.01)
  *A61P 27/16*      (2006.01)
(52) U.S. Cl.
  CPC ..... *A23V 2002/00* (2013.01); *A61K 2236/331* (2013.01); *A61K 2236/333* (2013.01)

(56)                References Cited

FOREIGN PATENT DOCUMENTS

| | | |
|---|---|---|
| JP | 2011-037738 A | 2/2011 |
| KR | 10-2010-0114349 A | 10/2010 |
| KR | 10-190412 B1 | 9/2018 |
| KR | 10-1905865 B1 | 10/2018 |

OTHER PUBLICATIONS

Medlineplus, Tinnitus, 2017, NIH: National Institute on Deafness and Other Communication Disorders, from https://medlineplus.gov/tinnitus.html (Year: 2017).*

Rabniowitz, P., Noise-Induced Hearing Loss, 2000, American Family Physician, 61, 1-15 (Year: 2000).*

Bombardelli et al., "Hypericum perforatum", Fitoterapia, 1995, vol. LXVI, No. 1, pp. 43-68 (26 pages total).

Nathan Zassman, et al., "Natural Solutions for Tinnitus Relief", AvivaHealth.com, Mar. 25, 2016, pp. 1-8, <URL:https://www.avivahealth.com/blogs/articles/tinnitus-natural-cures-that-work>.

Carol A, Bauer, M.D., "Tinnitus", The New England Journal of Medicine, Mar. 29, 2018, pp. 1224-1231, vol. 378, No. 13.

James A. Henry, et al., "General Review of Tinnitus: Prevalence, Mechanisms, Effects, and Management", Journal of Speech, Language, and Hearing Research, Oct. 2005, pp. 1204-1235, vol. 48.

Alexander Von Boetticher, "Ginkgo biloba extract in the treatment of tinnitus: a systematic review", Neuropsychiatric Disease and Treatment, 2011, pp. 441-447 vol. 7.

M.P. Hilton, et al., "The Cochrane Collaboration", Cochrane Database System Rev., 2004, pp. 1-20, vol. 2, CD003852.

Debasis Bagchi, et al., "Free radicals and grape seed proanthocyanidin extract: importance in human health and disease prevention", Toxicology, 2000, pp. 187-197, vol. 148.

Y. Curin, et al., "Cellular Mechanisms of the Protective Effect of Polyphenols on the Neurovascular Unit in Strokes", Cardiovasc. Hematol. Agents Med. Chem., Oct. 2006, pp. 277-288, vol. 4, No. 4.

International Search Report for PCT/KR2020/001964 dated Oct. 27, 2020 [PCT/ISA/210].

Written Opinion for PCT/KR2020/001964 dated Oct. 27, 2020 [PCT/ISA/237].

Korean Intellectual Property Office, Office Action for KR 10-2020-0017033 dated Apr. 10, 2021.

Worrall et al., "Tinnitus and Hyperacusis", Cummings Otolaryngology Seventh Edition Head and Neck Surgery, May 11, 2020, pp. 2328-2341.e5.

Le Prell, "Noise-Induced Hearing Loss", Cummings Otolaryngology Seventh Edition Head and Neck Surgery, May 11, 2020, pp. 2342-2355.e4.

* cited by examiner

COMPOSITION FOR PREVENTING OR TREATING TINNITUS COMPRISING *VITIS VINIFERA* LEAF EXTRACT AS ACTIVE INGREDIENT

CROSS REFERENCE TO RELATED APPLICATIONS

This application is a National Stage of International Application No. PCT/KR2020/001964 filed Feb. 12, 2020, claiming priority based on Korean Patent Application No. 10-2019-0015991 filed Feb. 12, 2019.

TECHNICAL FIELD

The present invention relates to a composition for preventing or treating tinnitus, and more particularly, to a pharmaceutical composition and a food composition for preventing or treating tinnitus comprising a *Vitis vinifera* leaf extract as an active ingredient.

BACKGROUND ART

Tinnitus (ringing of the ears) is a symptom in which a person hears a sound even in the absence of external sound stimulus. Although the sound is usually described as ringing of the ears, the sound is felt on the inside or outside of the head, and may occur in only one ear or in both ears. Tinnitus appears as a buzzing, hissing, growling, cicada-like sound, or a sound having a fixed pitch (Bauer C. A., N. Engl. J. Med. 2018 Mar. 29; 378(13):1224-1231). Such tinnitus occurs in about 10-15% of adults (Henry J. A. et al., J. Speech Lang. Hear. Res. 2005 October; 48(5):1204-35). According to data from the Health Insurance Review and Assessment Service, the number of tinnitus patients increased by 15% from 281,351 to 324,392 over the four years from 2013 to 2017.

The pathophysiological characteristics of tinnitus are not fully understood, and the exact pathogenesis thereof is not known. For the treatment of tinnitus, the focus has been on alleviating tinnitus through rehabilitation to date, and no tinnitus medicine has been approved by the US Food and Drug Administration (FDA) to date.

The treatment of tinnitus is mainly carried out with drugs, and blood flow enhancement vasodilators are mainly prescribed, and antidepressants, anti-anxiety drugs, and drugs made from natural *Ginkgo biloba* are prescribed. It has been suggested that a medicament made from natural *Ginkgo biloba* contains an EGb 761 component extracted from *Ginkgo biloba* for use in the treatment of tinnitus by administration at a dose of 160 mg or more daily for 3 to 6 months (von Boetticher A., Neuropsychiatr. Dis. Treat. 2011; 7:441-7), and such a medicament is classified as a therapeutic aid for tinnitus by the Korean Health Insurance Review and Assessment Service, and is thus not eligible for health insurance benefits. Moreover, it has been reported in academia that the EGb 761 component extracted from *ginkgo* leaves is effective as a natural material for use in the treatment of tinnitus, but as shown in most studies, it is disadvantageous in that the performance thereof does not exceed that of a placebo (Hilton, M., Stuart, E., Cochrane Database Syst Rev. 2004; (2):CD003852).

Meanwhile, *Vitis vinifera* leaves are composed of many polyphenols, including anthocyanins, flavonoids, and organic acids (Bombardelli E., Morazzoni P., Fitoterapia. 1995; 66:43-68). One such polyphenol, proanthocyanidin, has been used for various purposes, such as antioxidants (Bagchi D. et al., Toxicology. 2000 Aug. 7; 148(2-3):187-97), nutritional supplements, and prevention of atherosclerosis and cardiovascular disease (Curin Y. et al., Cardiovasc. Hematol. Agents Med. Chem. 2006 October; 4(4):277-88).

It is known that the grape leaf extract has an antioxidant effect (Korean Patent Application Publication No. 10-2010-0114349) and that the *Vitis vinifera* leaf extract has an effect of treating noise-induced hearing loss (Korean Patent No. 10-1901412), but the effect thereof on preventing or treating tinnitus is not known.

Accordingly, the present inventor has made great efforts to develop a tinnitus medicine by focusing on the use of blood flow enhancement vasodilators as drugs for the treatment of tinnitus, and thus ascertained that a *Vitis vinifera* leaf extract (VLE), showing effects of prevention of atherosclerosis and cardiovascular disease, is able to notably alleviate tinnitus symptoms induced by exposure to noise, thereby culminating in the present invention.

The information described in the background section is only for improving understanding of the background of the present invention, and it is not to be construed as including information forming the related art already known to those skilled in the art to which the present invention belongs.

SUMMARY OF THE INVENTION

It is an object of the present invention to provide a pharmaceutical composition for preventing or treating tinnitus and a food composition for preventing or ameliorating tinnitus comprising a *Vitis vinifera* leaf extract capable of significantly alleviating or ameliorating tinnitus symptoms.

It is another object of the present invention to provide a method of preventing or treating tinnitus comprising administering a *Vitis vinifera* leaf extract to a subject.

It is still another object of the present invention to provide the use of the *Vitis vinifera* leaf extract for the prevention or treatment of tinnitus.

It is yet another object of the present invention to provide the use of the *Vitis vinifera* leaf extract for the manufacture of a medicament for the prevention or treatment of tinnitus.

In order to achieve the above and other objects, the present invention provides a pharmaceutical composition for preventing or treating tinnitus comprising a *Vitis vinifera* leaf extract as an active ingredient.

In addition, the present invention provides a method of preventing or treating tinnitus comprising administering a *Vitis vinifera* leaf extract to a subject.

In addition, the present invention provides the use of the *Vitis vinifera* leaf extract for the prevention or treatment of tinnitus.

In addition, the present invention provides the use of the *Vitis vinifera* leaf extract for the manufacture of a medicament for the prevention or treatment of tinnitus.

In addition, the present invention provides a food composition for preventing or ameliorating tinnitus comprising a *Vitis vinifera* leaf extract as an active ingredient.

3 administration of VLE for 1 week (D 9), and after administration of VLE for 2 weeks (D 16) through an auditory brainstem response test.

Figure 3:
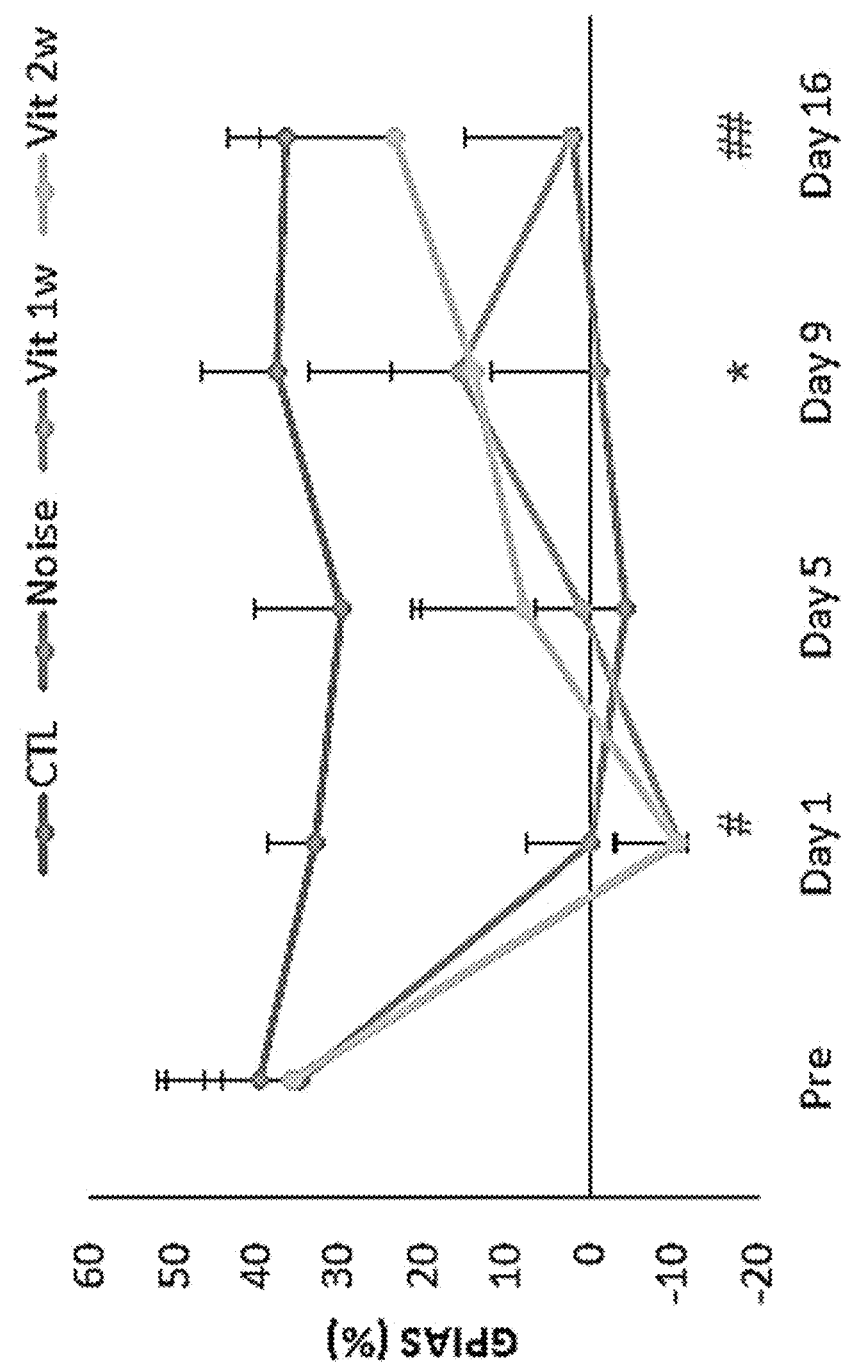

FIG. 3 shows verification of the effect of VLE on treating tinnitus through GPIAS analysis.

Figure 4:
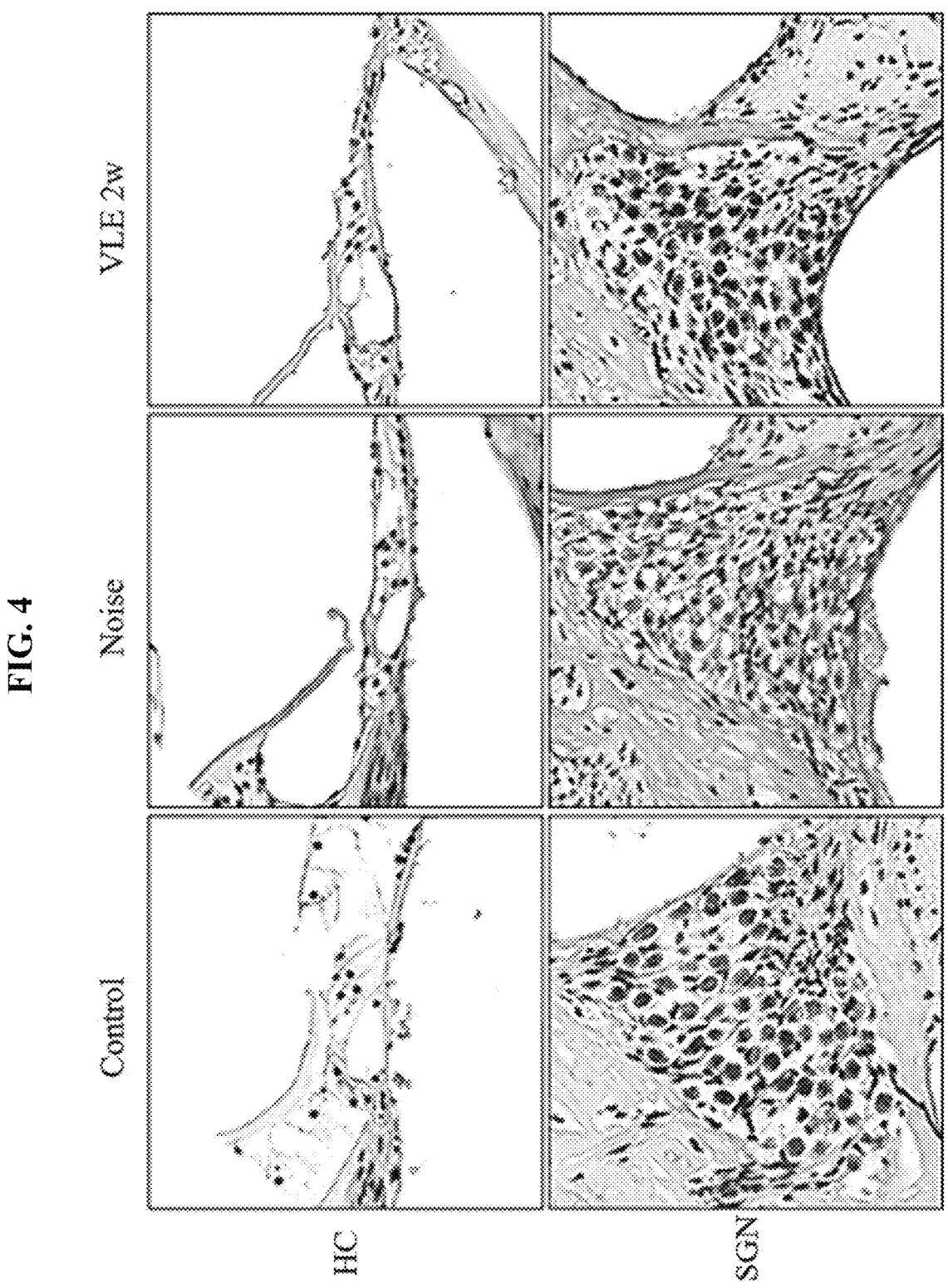

FIG. 4 shows the results of histological analysis of the presence of tinnitus and the therapeutic effect of VLE.

DETAILED DESCRIPTION AND PREFERRED EMBODIMENTS OF THE INVENTION

Unless otherwise defined, all technical and scientific terms used herein have the same meanings as those typically understood by those skilled in the art to which the present invention belongs. Generally, the nomenclature used herein is well known in the art and is typical.

In the present invention, after establishing an animal model of tinnitus induced by noise, an auditory brainstem response (ABR) test was conducted to confirm that hearing was not deteriorated by noise. Then, in order to confirm the effect of treating tinnitus, the established animal model of tinnitus was administered with a *Vitis vinifera* leaf extract, and gap-prepulse inhibition of acoustic startle (GPIAS) analysis and histological analysis were performed. As a result, it was confirmed that the noise-induced tinnitus symptoms were relieved by the *Vitis vinifera* leaf extract (VLE), and that the response to the tinnitus symptoms was ameliorated gradually when VLE was continuously administered.

Accordingly, an aspect of the present invention pertains to a pharmaceutical composition for preventing or treating tinnitus comprising a *Vitis vinifera* leaf extract as an active ingredient.

As used herein, the term "extract" refers to a substance obtained by being separated from *Vitis vinifera* leaves.

In the present invention, the *Vitis vinifera* leaf extract is obtained by extracting *Vitis vinifera* leaves with a solvent selected from the group consisting of water, a C1-C4 alcohol, and a mixed solvent of water and a C1-C4 alcohol. Preferably, the *Vitis vinifera* leaf extract of the present invention is obtained through extraction using water as a solvent.

The mixed solvent is preferably an aqueous solution of about 70% ethanol. Extraction may be performed using an extraction process known in the art, for example, cold extraction, hot-water extraction, ultrasonic extraction, reflux cooling extraction, etc., but is not limited thereto. The extraction temperature may be determined by selecting any temperature range suitable for the extraction process by those skilled in the art, and the extraction temperature may be, for example, 20° C. to 100° C. or the like, but is not limited thereto. In addition, the extraction time may vary depending on the extraction process, and may be appropriately selected by those skilled in the art, and extraction may be performed once or multiple times for about 1 hour to 10 days, but the present invention is not limited thereto. Preferably, the extraction is carried out 2 to 3 times for about 2 days each time at room temperature using the extraction solvent described above.

The dried *Vitis vinifera* leaf extract of the present invention comprises polyphenol as an active ingredient.

As used herein, the term "polyphenol" refers to a compound that has two or more aromatic hydroxyl groups and has high antioxidant ability to protect DNA from damage due to exposure to reactive oxygen species in vivo or to protect cellular proteins and enzymes, thereby lowering the risk of various diseases. Moreover, in addition to the well-known antioxidant effect, polyphenol is effective at ameliorating symptoms that may occur due to circulatory failure. It is known to be effective at eliminating swelling and discomfort caused by lower extremity venous insufficiency because it promotes a circulatory action by controlling capillary permeability, as well as increasing the elasticity of blood vessel walls by acting on blood vessels.

*Vitis viniferas* may have different uses depending on the extraction site thereof. In particular, a grape seed extract may be used for vasoprotection, and a grape leaf extract may be used specifically to treat varicose veins. Enteron in a tablet form, which is a *Vitis vinifera* seed extract having the effect of ameliorating symptoms of retinal and choroidal circulation, and Antax in a capsule form, which is a dried *Vitis vinifera* leaf extract having the effect of ameliorating symptoms of varicose veins, are approved as different medicines and used.

In the present invention, tinnitus is preferably caused by noise, drugs, or aging, but the present invention is not limited thereto.

The term "tinnitus" of the present invention may be classified into objective tinnitus that is capable of being heard from outside and subjective tinnitus that only a patient with tinnitus may hear, but which is inaudible externally. In addition, tinnitus may be classified into peripheral tinnitus and central tinnitus based on a difference in the method of perception by a patient. Peripheral (or cochlear) tinnitus is presumed to originate from the peripheral nervous system and cochlea, and central tinnitus is presumed to originate from the auditory cortex.

Subjective tinnitus may have several causes, and the most common cause is noise, specifically, exposure to excessive or loud noise. Subjective tinnitus is also known to occur as a side effect of some drugs, such as aspirin. Furthermore, it may occur as a side effect of natural hearing impairment due to aging, or hereditary (congenital) hearing impairment.

The *Vitis vinifera* leaf extract of the present invention is capable of effectively alleviating or ameliorating tinnitus induced by noise or the like.

In an embodiment, the dried *Vitis vinifera* leaf extract of the present invention was freeze-dried and stored in a powder form for use. The powder was dissolved in water and administered to each mouse at a concentration of 120 mg/kg, after which tinnitus induced by noise was analyzed through GPIAS (gap-prepulse inhibition of acoustic startle). As a result, it was confirmed that the GPIAS value was notably increased in all of the experimental groups administered with VLE compared to the control group, and also that the response to tinnitus symptoms was gradually ameliorated when VLE was continuously administered (FIG. 3). In addition, the effect of administration of VLE on treating tinnitus was verified through histological analysis (FIG. 4). This means that the noise-induced tinnitus symptoms were relieved by VLE.

As described above, the *Vitis vinifera* leaf extract of the present invention may be useful in the prevention, amelioration or treatment of noise-induced tinnitus.

Another aspect of the present invention pertains to a method of preventing or treating tinnitus comprising administering a *Vitis vinifera* leaf extract to a subject.

Still another aspect of the present invention pertains to the use of the *Vitis vinifera* leaf extract for the prevention or treatment of tinnitus.

Yet another aspect of the present invention pertains to the use of the *Vitis vinifera* leaf extract for the manufacture of a medicament for the prevention or treatment of tinnitus.

The composition of the present invention is administered in a pharmaceutically effective amount. As used herein, the term "pharmaceutically effective amount" refers to an amount that is sufficient to treat a disease with a reasonable benefit/risk ratio applicable to medical treatment, and the effective dose level may be determined depending on the subject, the severity of disease, age, gender, the activity of a drug, the sensitivity to a drug, the time of administration, the route of administration, the rate of excretion, the duration of treatment, factors including drugs taken concurrently therewith, and other factors well known in the medical field. The composition of the present invention may be administered as a therapeutic agent alone or in combination with other therapeutic agents, may be administered sequentially or simultaneously with conventional therapeutic agents, and may be administered once or multiple times. Taking all of the above factors into consideration, it is important to administer the composition capable of obtaining the maximum effect in a minimum amount without side effects, and such an amount may be easily determined by those skilled in the art.

The pharmaceutical composition of the present invention may comprise a pharmaceutically acceptable carrier, and may be formulated in the forms of oral formulations, external formulations, suppositories, and sterile injectable solutions, of powders, granules, tablets, capsules, suspensions, emulsions, syrups, aerosols, etc., in accordance with individual typical methods.

The pharmaceutically acceptable carrier includes, but is not limited to, those commonly used in the art, such as lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil. In addition, the pharmaceutical composition of the present invention comprises a diluent or excipient such as a filler, an extender, a binder, a wetting agent, a disintegrant, a surfactant, etc., and other pharmaceutically acceptable additives.

When the pharmaceutical composition of the present invention is manufactured in the form of a solid formulation for oral administration, examples of the solid formulation may include tablets, pills, powders, granules, capsules, etc., and the solid formulation may include at least one excipient, for example, starch, calcium carbonate, sucrose, lactose, gelatin, and the like, and may also include lubricants such as magnesium stearate and talc, but the present invention is not limited thereto.

When the pharmaceutical composition of the present invention is manufactured in the form of a liquid formulation for oral administration, examples of the liquid formulation may include suspensions, internal solutions, emulsions, syrups, and the like, and the liquid formulation may include diluents such as water, liquid paraffin, etc., wetting agents, sweeteners, fragrances, preservatives, and the like, but the present invention is not limited thereto.

When the pharmaceutical composition of the present invention is manufactured in the form of a formulation for parenteral administration, examples of such a formulation may include sterile aqueous solutions, non-aqueous solvents, suspensions, emulsions, freeze-dried formulations, and suppositories, and non-aqueous solvents and suspensions include propylene glycol, polyethylene glycol, vegetable oils such as olive oil, injectable esters such as ethyl oleate, and the like, but the present invention is not limited thereto. The base of a suppository may include, but is not limited to, Witepsol, Macrogol, Tween 61, cacao butter, laurin, glycerogelatin, and the like.

The pharmaceutical composition of the present invention may be administered orally or parenterally (e.g. intravenously, subcutaneously, intraperitoneally, or topically) depending on the desired method, and the dose thereof may vary depending on the condition of a patient, the weight of a patient, the severity of disease, the form of a drug, and the route and time of administration, but it may be appropriately selected by those skilled in the art.

The dose of the *Vitis vinifera* leaf extract comprised in the pharmaceutical composition of the present invention may vary depending on the condition, weight, age, etc. of a patient, the severity of disease, the form of a drug, and the route and time of administration, but may be appropriately selected by those skilled in the art. For example, the *Vitis vinifera* leaf extract may be administered in a dose of 1 to 2000 mg/kg per day, and preferably 10 to 2000 mg/kg per day, and the administration may be carried out once or several times a day.

A further aspect of the present invention pertains to a food composition for preventing or ameliorating tinnitus comprising a *Vitis vinifera* leaf extract as an active ingredient.

In the present invention, the *Vitis vinifera* leaf extract is obtained by extracting *Vitis vinifera* leaves with a solvent selected from the group consisting of water, a C1-C4 alcohol, and a mixed solvent of water and a C1-C4 alcohol.

In the present invention, the tinnitus is preferably caused by noise, drugs, or aging, but the present invention is not limited thereto.

The food composition of the present invention may be used as a functional health food. As used herein, the term "functional health food" refers to a food manufactured and processed using materials or components having functionality useful for the human body according to Act No. 6727 on Functional Health Foods, and the term "functionality" refers to intake purporting to obtain good health effects such as nutrient control for the structure and function of the human body or a physiological action.

The food composition of the present invention may comprise a typical food additive, and the suitability as the "food additive" is determined based on standards and criteria for relevant items according to general rules and general test methods of the Food Additives Code approved by the Ministry of Food and Drug Safety, unless otherwise specified.

Examples of the items listed in the "Food Additives Code" may include chemical compounds such as ketones, glycine, potassium citrate, nicotinic acid, cinnamic acid, etc., natural additives such as persimmon color, licorice extract, crystalline cellulose, Kaoliang color, guar gum, etc., and mixed formulations such as sodium L-glutamate formulations, alkali additives for noodles, preservative formulations, tar color formulations, etc.

The food composition of the present invention may comprise the *Vitis vinifera* leaf extract in an amount of 0.01 to 95 wt %, and preferably 1 to 80 wt %, based on the total weight of the composition, in order to prevent and/or ameliorate tinnitus, particularly noise-induced tinnitus.

Moreover, the food composition of the present invention may be manufactured and processed in the form of tablets, capsules, powders, granules, liquids, pills, etc., in order to prevent and/or ameliorate hearing loss.

For example, a functional health food in a tablet form may be manufactured in a manner in which the *Vitis vinifera* leaf extract, or a mixture thereof with an excipient, a binder, a disintegrant, and other additives, is granulated through a typical process, added with a lubricant or the like, and then compacted, or the mixture may be directly compacted. Also, the functional health food in a tablet form may contain a flavor enhancer, etc., or may be coated with a suitable coating agent, as necessary.

Among functional health foods in the form of capsules, a hard capsule may be manufactured by filling a typical hard capsule with a mixture of the *Vitis vinifera* leaf extract and an additive such as an excipient, etc., or granules or coated granules thereof, and a soft capsule may be manufactured by filling a capsule base such as gelatin with a mixture of the *Vitis vinifera* leaf extract and an additive such as an excipient, etc. The soft capsule may contain a plasticizer such as glycerin or sorbitol, a colorant, a preservative, and the like, as necessary.

A functional health food in a pill form may be manufactured by shaping a mixture of the *Vitis vinifera* leaf extract, an excipient, a binder, a disintegrant, etc. in an appropriate manner, and as necessary, the pill may be coated with white sugar or an additional suitable coating agent, or with starch, talc, or a suitable material.

A functional health food in a granular form may be manufactured by granulating a mixture of the *Vitis vinifera* leaf extract, an excipient, a binder, a disintegrant, etc. in an appropriate manner, and may contain a fragrance, a flavor enhancer, etc., as necessary. For the functional health food in a granular form, when the particle size test is performed using No. 12 (1680 µm), No. 14 (1410 µm), and No. 45 (350 µm) sieves, all of the granules may pass through a No. 12 sieve, 50% or less of the total amount thereof may remain on a No. 14 sieve, and 150% or less of the total amount thereof may pass through a No. 45 sieve.

The excipient, binder, disintegrant, lubricant, flavor enhancer, fragrance, etc. are defined as including those having the same or similar functions as described in literature known in the art (The Korean Pharmacopoeia review, Moonseongsa, Korea Pharmacy University Council, $5^{th}$ ed., p 33-48, 1989).

EXAMPLES

Hereinafter, the present invention will be described in more detail with reference to examples. These examples are merely set forth to illustrate the present invention, and are not to be construed as limiting the scope of the present invention, as will be apparent to those skilled in the art.

Example 1: Preparation of *Vitis vinifera* Leaf Extract (VLE)

A *Vitis vinifera* leaf extract was purchased from Finzelberg GmbH & Co. Alternatively, it is obtained by extracting *Vitis vinifera* leaves with a solvent such as water, a C1-C4 alcohol or a mixed solvent of water and a C1-C4 alcohol, preferably water, as a solvent.

The mixed solvent is preferably an aqueous solution of about 70% ethanol. Extraction may be performed through an extraction process known in the art, for example, cold extraction, hot-water extraction, ultrasonic extraction, reflux cooling extraction, and the like. The extraction temperature may be, for example, 20° C. to 100° C. or the like. Also, the extraction time may vary depending on the extraction process, and extraction may be performed once or multiple times for about 1 hour to 10 days. Preferably, extraction is carried out 2 to 3 times for about 2 days each time at room temperature using the extraction solvent described above.

After extraction, the *Vitis vinifera* leaf extract was dissolved in water to a concentration of 120 mg/kg.

Example 2: Noise-Induced Tinnitus Animal Model 8-week-old male Sprague-Dawley rats (250-300 g) were bred under a light/dark cycle of 12 hours (lighting from 8 o'clock a.m. to 8 o'clock p.m.) at a temperature of 23±2° C. and humidity-controlled conditions. Water and food were freely fed.

Groups were divided into a control group, a noise group, a group administered with the dried *Vitis vinifera* leaf extract (VLE) for 1 week after exposure to noise (Vit 1 w group), and a group administered with VLE for 2 weeks after exposure to noise (Vit 2 w group). VLE was prepared at a concentration of 120 mg/kg using tap water and then orally administered using an oral zonde needle, and tap water was orally administered to the noise group.

The total period of exposure to noise was 1 day, and the rats were exposed to narrow-band noise at 16 kHz (having a bandwidth of 100 Hz) at a sound pressure of 112 dB for 4 hours. For noise exposure, a sound source device (Sine Random Generator Type 1027, Bruel & Kjær, Denmark), an amplifier (R300 plus amplifier, Inter-M, Korea), a speaker (#84234xx, Electro0voice, USA), and a shield were used.

Tinnitus analysis was performed before the start of the experiment and on the $1^{st}$, $5^{th}$, $9^{th}$, and $16^{th}$ days after exposure to noise using a gap-prepulse inhibition of acoustic startle (GPIAS) measurement device. Each rat was placed in an acoustically transparent enclosure in a chamber. The enclosure of the chamber is in a wire-mesh form to allow sound to pass therethrough, and the bottom of the chamber is equipped with an accelerometer sensor that is able to detect the startle reflex. All tinnitus measurements were performed in a soundproof room.

For the GPIAS process, 20 gap stimuli and 20 no-gap stimuli were applied to each rat. The sequence of stimuli was randomized, and the inter-stimulus interval (ISI) between the main stimulus pulses applied to each animal was also randomly selected within the range of 17 to 23 seconds. The background sound was set such that narrow-band noise of 16 kHz was emitted at 60 dB SPL, and the silence interval was set to 50 ms during gap stimulation. The main stimulus pulse sound for the startle reflex (SR) was white noise at 110 dB SPL for 50 ms.

Example 3: Auditory Brainstem Response Test in Tinnitus Animal Model

The auditory brainstem response (ABR) test was conducted to determine a decrease in hearing, because the decrease in hearing during GPIAS measurement before and after exposure to noise reduces the reliability of the GPIAS measurement value.

This was performed after anesthesia with Zoletil 50. The minimum stimulus sound level (dB) at which a waveform of wave V was formed by applying tone burst sounds of 8 kHz, 16 kHz, and 32 kHz was determined to be a hearing threshold.

The hearing threshold values before exposure to noise were less than 15 dB SPL at 8, 16, and 32 kHz in all of the control group and the three experimental groups.

1 day after exposure to noise, the hearing threshold value at 16 kHz was measured to be 18.0±6.9 dB SPL in the noise group, 17.8±7.1 dB SPL in the group administered with VLE for 1 week after exposure to noise (Vit 1 w group), and 18.8±5.0 dB SPL in the group administered with VLE for 2 weeks after exposure to noise (Vit 2 w group). Also, the hearing threshold value at 32 kHz was measured to be 14.2±4.2 dB SPL in the noise group, 13.8±4.7 dB SPL in the Vit 1 w group, and 16.3±5.6 dB SPL in the Vit 2 w group.

After oral administration of VLE for 1 week, the hearing threshold value at 16 kHz was measured to be 15.2±5.9 dB SPL in the noise group, 12.8±2.6 dB SPL in the Vit 1 w group, and 20.0±6.6 dB SPL in the Vit 2 w group, and the hearing threshold value at 32 kHz was measured to be 12.8±4.2 dB SPL in the noise group, 11.9±2.5 dB SPL in the Vit 1 w group, and 16.6±5.1 dB SPL in the Vit 2 w group.

Figure 2:
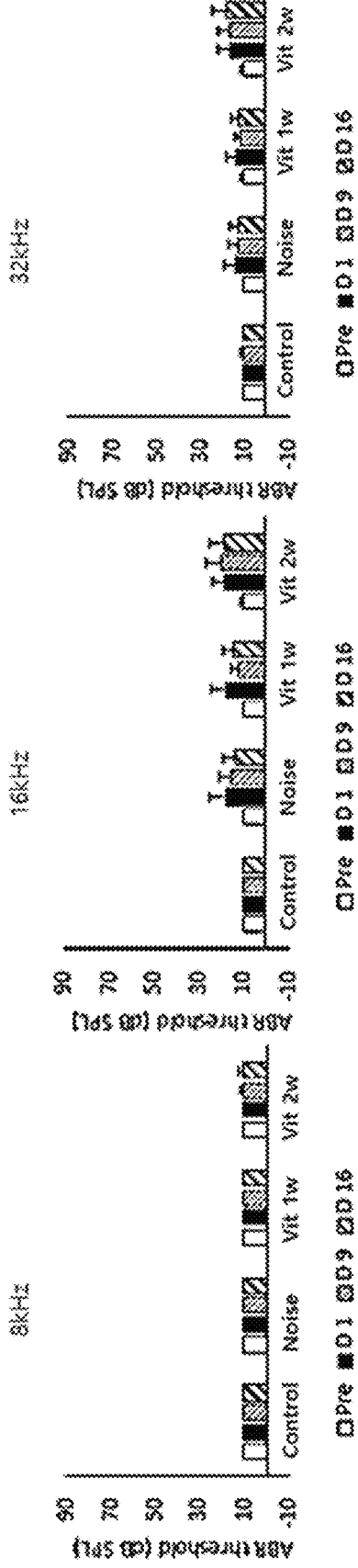
FIG. 2 shows changes in a hearing threshold before noise exposure (Pre), immediately after noise exposure (D 1), after

Therefore, it was confirmed that there was no hearing loss by maintaining a hearing threshold value of 20 dB SPL or less on average, even after exposure to noise (FIG. 2).

Example 4: Effect of *Vitis vinifera* Leaf Extract on Treatment of Tinnitus

Figure 1:
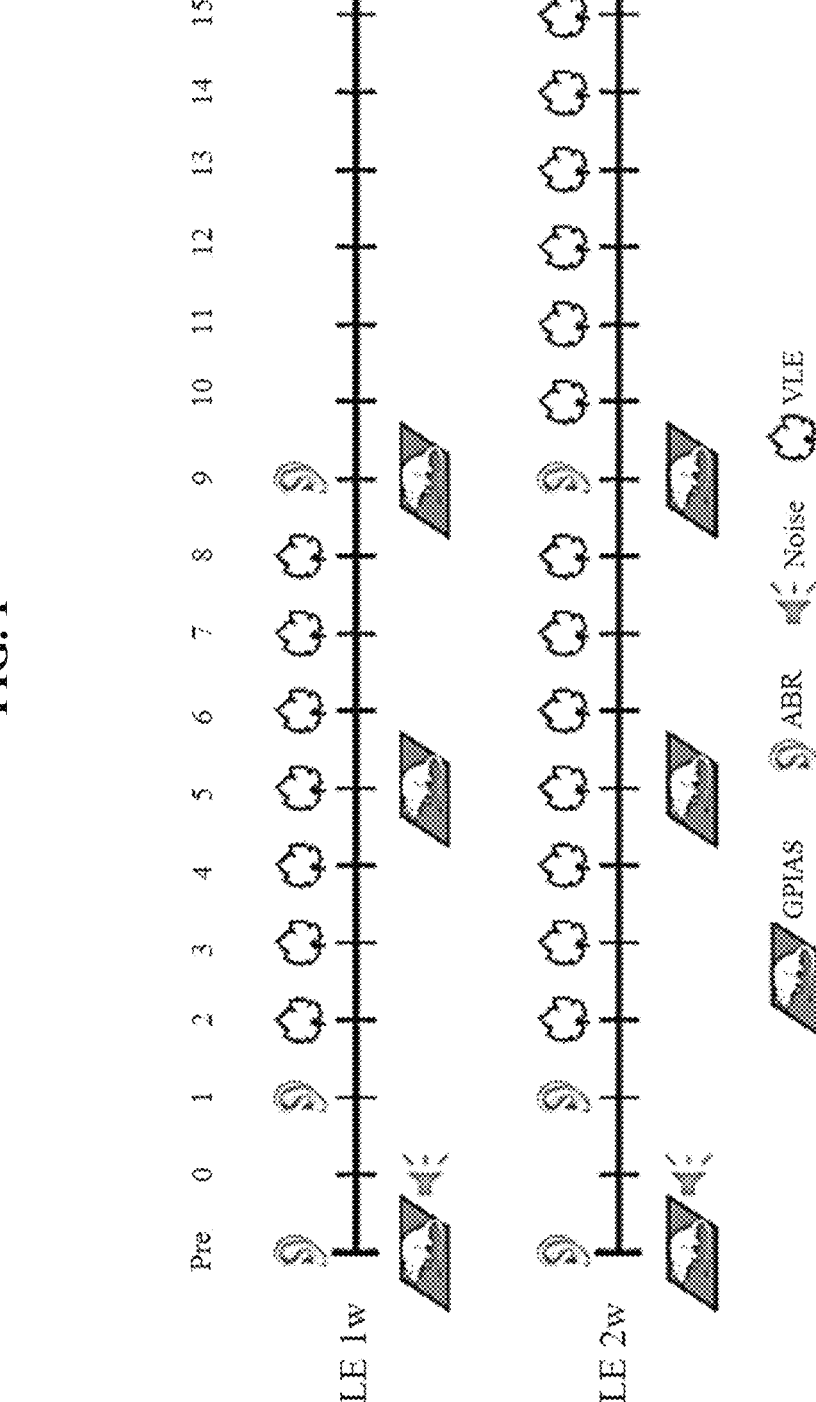
FIG. 1 shows a schedule for measurement of ABR (auditory brainstem response), GPIAS (gap-prepulse inhibition of acoustic startle), and administration of VLE (*Vitis vinifera* leaf extract).

A schedule of the auditory brainstem response (ABR) test, gap-prepulse inhibition of acoustic startle (GPIAS), and administration of the dried *Vitis vinifera* leaf extract (VLE) of Examples 2 and 3 is shown in FIG. 1.

For the four groups of Example 2, the average GPIAS value of the rats before exposure to noise was 39.7±12.3% in the control group, 34.8±9.2% in the noise group, 35.8±15.0% in the Vit 1 w group, and 35.7±10.7% in the Vit 2 w group. There was no statistically significant difference between the four groups.

1 day after exposure to noise and after administration of VLE for 3 days, 1 week, and 2 weeks, the average GPIAS values were compared in the four groups.

The average GPIAS value immediately after exposure to noise was measured to be −0.2±7.8% in the noise group and −10.6±7.8% in the Vit 1 w group, indicating that the value for the noise group was significantly high (p=0.013). After administration of VLE for 1 week, the value was measured to be −1.0±12.8% in the noise group and 15.9±7.9% in the Vit 1 w group, indicating that the value for the Vit 1 w group was significantly increased (p=0.026). However, when administration of VLE was stopped, the value was measured to be 2.1±13.1% in the noise group and 2.3±12.8% in the Vit 1 w group, indicating that there was no statistically significant difference between the two groups.

Meanwhile, the average GPIAS value immediately after exposure to noise between the noise group and the Vit 2 w group was measured to be −0.2±7.8% in the noise group and −10.3±7.1% in the Vit 2 w group, indicating that the value for the noise group was significantly high (p=0.016). After administration of VLE for 1 week, the value was measured to be −1.0±12.8% in the noise group and 14.2±19.4% in the Vit 2 w group, indicating that the value for the Vit 2 w group was increased (p=0.054), and when the administration of VLE was continued, the value was measured to be 2.1±13.1% in the noise group and 23.6±15.9% in the Vit 2 w group, indicating that the value for the Vit 2 w group was significantly increased (p=0.002) (FIG. 3).

Thereafter, it was confirmed that the GPIAS value was notably increased in both of the two experimental groups to which VLE was administered compared to the control group. This means that the noise-induced tinnitus symptoms were relieved by VLE. Specifically, when administration of VLE was stopped 1 week after induction of tinnitus, tinnitus was observed again, and when VLE was continuously administered, it was confirmed that the response to tinnitus symptoms was gradually ameliorated.

Example 5: Histological Analysis of Effect of *Vitis vinifera* Leaf Extract on Treatment of Tinnitus H&E staining was performed for histological analysis in order to confirm the effect of the *Vitis vinifera* leaf extract (VLE) on treatment of tinnitus. The control group, the noise group, and the group administered with VLE for 2 weeks after exposure to noise (Vit 2 w group) of Example 2 were used.

There was no difference in the shape or number of hair cells (HC) between the groups, but in spiral ganglion neurons (SGN), the size of the nucleus of the noise group was smaller than that of the control group. In comparison, the shape of the nucleus in the VLE 2 w group was similar to that of the control group (FIG. 4).

INDUSTRIAL APPLICABILITY

A composition comprising the *Vitis vinifera* leaf extract as an active ingredient according to the present invention, is very effective at alleviating and ameliorating tinnitus induced by noise and the like, and is thus remarkably useful as a composition for preventing or treating tinnitus.

Although specific embodiments of the present invention have been disclosed in detail as described above, it will be obvious to those skilled in the art that the description is merely of preferable exemplary embodiments, and is not to be construed as limiting the scope of the present invention. Therefore, the substantial scope of the present invention will be defined by the appended claims and equivalents thereof.

The invention claimed is:

1. A method of treating noise-induced tinnitus in a subject in need thereof comprising administering an effective amount of a composition consisting of a *Vitis vinifera* leaf extract as an active ingredient to the subject.

2. The method of claim 1, wherein the *Vitis vinifera* leaf extract is obtained by extracting *Vitis vinifera* leaves with a solvent selected from the group consisting of water, a C1-C4 alcohol, and a mixed solvent of water and a C1-C4 alcohol.

3. The method of claim 1, wherein the composition is a pharmaceutical composition.

4. The method of claim 1, wherein the composition is a food stuff or a dietary supplement.

* * * * *